(12) United States Patent
Jaeschke et al.

(10) Patent No.: US 8,530,472 B2
(45) Date of Patent: Sep. 10, 2013

(54) ETHYNYL DERIVATIVES

(71) Applicant: Hoffmann-La Roche Inc., Nutley, NJ (US)

(72) Inventors: Georg Jaeschke, Basel (CH); Lothar Lindemann, Basel (CH); Antonio Ricci, Birsfelden (CH); Daniel Rueher, Raedersdorf (FR); Heinz Stadler, Basel (CH); Eric Vieira, Frekendorf (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/628,128

(22) Filed: Sep. 27, 2012

(65) Prior Publication Data

US 2013/0090347 A1    Apr. 11, 2013

(30) Foreign Application Priority Data

Oct. 7, 2011  (EP) .................................. 11184257

(51) Int. Cl.
| | | |
|---|---|---|
| *A61K 31/505* | (2006.01) | |
| *A61K 31/50* | (2006.01) | |
| *A61K 31/44* | (2006.01) | |
| *C07D 237/02* | (2006.01) | |
| *C07D 239/02* | (2006.01) | |
| *C07D 211/00* | (2006.01) | |

(52) U.S. Cl.
USPC ........... 514/247; 514/275; 514/352; 544/224; 544/332; 546/312

(58) Field of Classification Search
USPC .................. 514/247, 275, 352; 544/224, 332; 546/312
See application file for complete search history.

(56) References Cited

U.S. PATENT DOCUMENTS

2009/0042855 A1    2/2009    Conn et al.

FOREIGN PATENT DOCUMENTS

| WO | 2006/044823 | 4/2006 |
| WO | 2006/099972 | 9/2006 |
| WO | 2010/012740 | 2/2010 |

OTHER PUBLICATIONS

Chem Abstracts Chemcats (XP-002687600),:1 (Sep. 5, 2012).
(International Search Report for PCT/EP2012/069605 Dec. 21, 2012).
Varnes et al., Bioorganic & Medicinal Chem Letters 21:1402-1406 (2011).

*Primary Examiner* — Samantha Shterengarts

(57) ABSTRACT

The present invention relates to ethynyl derivatives of formula I

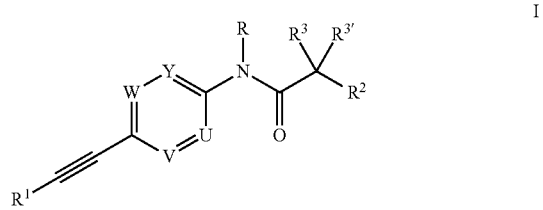

wherein U, V, W, Y, R, $R^1$, $R^2$, $R^3$ and $R^{3'}$ are as described herein.

It has been found that the compounds of general formula I are allosteric modulators of the metabotropic glutamate receptor subtype 5 (mGluR5).

13 Claims, No Drawings

ETHYNYL DERIVATIVES

PRIORITY TO RELATED APPLICATION(S)

This application claims the benefit of European Patent Application No. 11184257.1, filed Oct. 7, 2011, which is hereby incorporated by reference in its entirety.

FIELD OF THE INVENTION

In the central nervous system (CNS) the transmission of stimuli takes place by the interaction of a neurotransmitter, which is sent out by a neuron, with a neuroreceptor.

Glutamate is the major excitatory neurotransmitter in the brain and plays a unique role in a variety of central nervous system (CNS) functions. The glutamate-dependent stimulus receptors are divided into two main groups. The first main group, namely the ionotropic receptors, forms ligand-controlled ion channels. The metabotropic glutamate receptors (mGluR) belong to the second main group and, furthermore, belong to the family of G-protein coupled receptors.

At present, eight different members of these mGluR are known and of these some even have sub-types. According to their sequence homology, signal transduction mechanisms and agonist selectivity, these eight receptors can be sub-divided into three sub-groups:

mGluR1 and mGluR5 belong to group I, mGluR2 and mGluR3 belong to group II and mGluR4, mGluR6, mGluR7 and mGluR8 belong to group III.

Ligands of metabotropic glutamate receptors belonging to the first group can be used for the treatment or prevention of acute and/or chronic neurological disorders such as psychosis, epilepsy, schizophrenia, Alzheimer's disease, cognitive disorders and memory deficits, as well as chronic and acute pain.

Other treatable indications in this connection are restricted brain function caused by bypass operations or transplants, poor blood supply to the brain, spinal cord injuries, head injuries, hypoxia caused by pregnancy, cardiac arrest and hypoglycaemia. Further treatable indications are ischemia, Huntington's chorea, amyotrophic lateral sclerosis (ALS), dementia caused by AIDS, eye injuries, retinopathy, idiopathic parkinsonism or parkinsonism caused by medicaments as well as conditions which lead to glutamate-deficiency functions, such as e.g. muscle spasms, convulsions, migraine, urinary incontinence, nicotine addiction, opiate addiction, anxiety, vomiting, dyskinesia and depressions.

Disorders mediated full or in part by mGluR5 are for example acute, traumatic and chronic degenerative processes of the nervous system, such as Alzheimer's disease, senile dementia, Parkinson's disease, Huntington's chorea, amyotrophic lateral sclerosis and multiple sclerosis, psychiatric diseases such as schizophrenia and anxiety, depression, pain and drug dependency (*Expert Opin. Ther. Patents* (2002), 12, (12)).

A new avenue for developing selective modulators is to identify compounds which act through allosteric mechanism, modulating the receptor by binding to a site different from the highly conserved orthosteric binding site. Allosteric modulators of mGluR5 have emerged recently as novel pharmaceutical entities offering this attractive alternative. Allosteric modulators have been described, for example in WO2008/151184, WO2006/048771, WO2006/129199 and WO2005/044797 and in *Molecular Pharmacology*, 40, 333-336, 1991; *The Journal of Pharmacology and Experimental Therapeutics, Vol* 313, *No.* 1, 199-206, 2005;

In recent years there have been significant advantages in understanding the pathophysiology of several disorders of brain development, suggesting that protein synthesis at synapses is triggered by activation of group I metabotropic glutamate receptors. Such disorders include fragile X syndrome, autism, idiopathic autism, tuberous sclerosis complex disorder, neurofibromatosis type 1 or Rett syndrome (*Annu. Rev. Med.,* 2011, 62, 31.1-31.19 and *Neuroscience* 156, 2008, 203-215).

Described in the prior art are positive allosteric modulators. They are compounds that do not directly activate receptors by themselves, but markedly potentiate agonist-stimulated responses, increase potency and maximum of efficacy. The binding of these compounds increases the affinity of a glutamate-site agonist at its extracellular N-terminal binding site. Allosteric modulation is thus an attractive mechanism for enhancing appropriate physiological receptor activation. There is a scarcity of selective allosteric modulators for the mGluR5 receptor. Conventional mGluR5 receptor modulators typically lack satisfactory aqueous solubility and exhibit poor oral bioavailability.

Therefore, there remains a need for compounds that overcome these deficiencies and that effectively provide selective allosteric modulators for the mGluR5 receptor.

SUMMARY OF THE INVENTION

The present invention relates to ethynyl derivatives of formula I

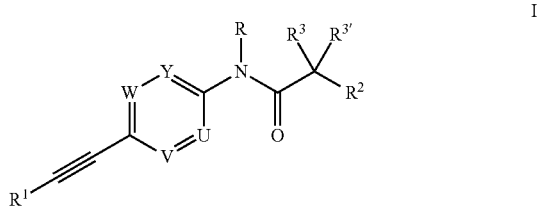

wherein U, V, W, Y, R, $R^1$, $R^2$, $R^3$ and $R^{3'}$ are as described below.

It has now been found that the compounds of general formula I are allosteric modulators of the metabotropic glutamate receptor subtype 5 (mGluR5).

DETAILED DESCRIPTION OF THE INVENTION

The present invention relates to ethynyl derivatives of formula I

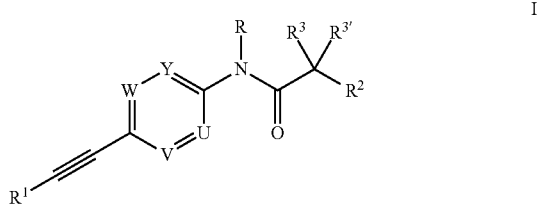

wherein
Y is N or CH; with the proviso that Y can only be CH, if at least one of U, V or W are N;
U is N or C—$R^4$;
V and W are independently N or CH;

with the proviso that only one of U, V or W can be simultaneously nitrogen;
R⁴ is hydrogen, methyl or halogen;
R¹ is phenyl or heteroaryl, which are optionally substituted by halogen, lower alkyl or lower alkoxy;
R is hydrogen or lower alkyl;
R² is hydrogen, lower alkyl, lower alkoxy, CF₃ or S-lower alkyl;
R³/R³' are independently from each other hydrogen, lower alkyl or lower alkoxy;
or R³ and R³' form together a C₃₋₅-cycloalkyl-, tetrahydrofuran- or an oxetane-ring;
or to a pharmaceutically acceptable acid addition salt, to a racemic mixture, or to its corresponding enantiomer and/or optical isomer and/or stereoisomer thereof.

The present invention relates to compounds of formula I and to their pharmaceutically acceptable salts, in cases where this applies to mixtures of enantiomers or diastereomers or their enantiomerically or diastereomerically pure forms, to these compounds as pharmaceutically active substances, to the processes for their production as well as to the use in the treatment or prevention of disorders, relating to allosteric modulators for the mGluR5 receptor, such as schizophrenia, cognition, fragile X syndrome or autism, and to pharmaceutical compositions containing the compounds of formula.

Compounds of formula I are distinguished by having valuable therapeutic properties. They can be used in the treatment or prevention of disorders, relating to allosteric modulators for the mGluR5 receptor.

The most preferred indications for compounds which are allosteric modulators are schizophrenia and cognition.

One embodiment of the invention are compounds of formula I-1

I-1 wherein
Y is N;
U is —CH— or N;
V and W are independently N or CH;
with the proviso that only one of U, V or W can be simultaneously nitrogen;
R¹ is phenyl, which is optionally substituted by halogen;
R is hydrogen or lower alkyl;
R² is lower alkyl, lower alkoxy, CF₃ or S-lower alkyl;
R³/R³' are independently from each other hydrogen or lower alkyl;
or a pharmaceutically acceptable acid addition salt, a racemic mixture, or its corresponding enantiomer and/or optical isomer and/or stereoisomer thereof.

Compounds of formula I-1 are the following:
2,2-Dimethyl-N-(5-phenylethynyl-pyridin-2-yl)-propionamide,
N-(5-Phenylethynyl-pyridin-2-yl)-butyramide,
Pentanoic acid (5-phenylethynyl-pyridin-2-yl)-amide,
3-Methyl-N-(5-phenylethynyl-pyridin-2-yl)-butyramide,
(RS)-2-Methyl-pentanoic acid (5-phenylethynyl-pyridin-2-yl)-amide,
2-Methylsulfanyl-N-(5-phenylethynyl-pyridin-2-yl)-acetamide,
2,2-Dimethyl-N-(5-phenylethynyl-pyrimidin-2-yl)-propionamide,
2,2,N-Trimethyl-N-(5-phenylethynyl-pyrimidin-2-yl)-propionamide,
2,2-Dimethyl-N-(6-phenylethynyl-pyridazin-3-yl)-propionamide,
2-Methoxy-N-(5-phenylethynyl-pyridin-2-yl)-acetamide,
N-[5-(3-Fluoro-phenylethynyl)-pyridin-2-yl]-2,2-dimethyl-propionamide,
2-Methoxy-2-methyl-N-(5-phenylethynyl-pyridin-2-yl)-propionamide,
N-[5-(3-Fluoro-phenylethynyl)-pyridin-2-yl]-2-methoxy-2-methyl-propionamide,
—N-[5-(2,5-Difluoro-phenylethynyl)-pyridin-2-yl]-2-methoxy-2-methyl-propionamide,
N-[5-(3-Chloro-phenylethynyl)-pyridin-2-yl]-3,3,3-trifluoro-2,2-dimethyl-propionamide or
N-[6-(3-Chloro-phenylethynyl)-pyridazin-3-yl]-2,2-dimethyl-propionamide.

One embodiment of the invention are compounds of formula IA

IA wherein
R¹ is phenyl or heteroaryl, which are optionally substituted by halogen, lower alkyl or lower alkoxy;
R is hydrogen or lower alkyl;
R² is hydrogen, lower alkyl, lower alkoxy, CF₃ or S-lower alkyl;
R³/R³' are independently from each other hydrogen, lower alkyl or lower alkoxy;
or R³ and R³' form together a C₃₋₅-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

Examples of compounds of formula IA are the following:
2,2-Dimethyl-N-(5-phenylethynyl-pyridin-2-yl)-propionamide,
N-(5-Phenylethynyl-pyridin-2-yl)-butyramide,
Pentanoic acid (5-phenylethynyl-pyridin-2-yl)-amide,
3-Methyl-N-(5-phenylethynyl-pyridin-2-yl)-butyramide,
(RS)-2-Methyl-pentanoic acid (5-phenylethynyl-pyridin-2-yl)-amide,
2-Methylsulfanyl-N-(5-phenylethynyl-pyridin-2-yl)-acetamide,
2-Methoxy-N-(5-phenylethynyl-pyridin-2-yl)-acetamide,
N-[5-(3-Fluoro-phenylethynyl)-pyridin-2-yl]-2,2-dimethyl-propionamide,
2-Methoxy-2-methyl-N-(5-phenylethynyl-pyridin-2-yl)-propionamide,
N-[5-(3-Fluoro-phenylethynyl)-pyridin-2-yl]-2-methoxy-2-methyl-propionamide,
N-[5-(2,5-Difluoro-phenylethynyl)-pyridin-2-yl]-2-methoxy-2-methyl-propionamide or N-[5-(3-Chloro-phenyl ethynyl)-pyridin-2-yl]-3,3,3-trifluoro-2,2-dimethyl-propionamide.

A further embodiment of the invention are compounds of formula IB

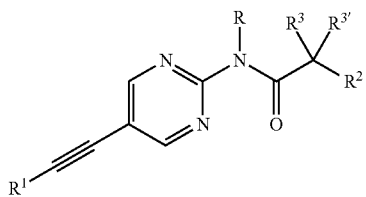

wherein
$R^1$ is phenyl or heteroaryl, which are optionally substituted by halogen, lower alkyl or lower alkoxy;
R is hydrogen or lower alkyl;
$R^2$ is hydrogen, lower alkyl, lower alkoxy, $CF_3$ or S-lower alkyl;
$R^3/R^{3'}$ are independently from each other hydrogen, lower alkyl or lower alkoxy;
or $R^3$ and $R^{3'}$ form together a $C_{3-5}$-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

Specific examples from compounds of formula IB are the following:
2,2-Dimethyl-N-(5-phenylethynyl-pyrimidin-2-yl)-propionamide or
2,2,N-Trimethyl-N-(5-phenylethynyl-pyrimidin-2-yl)-propionamide.

A further embodiment of the invention are compounds of formula IC

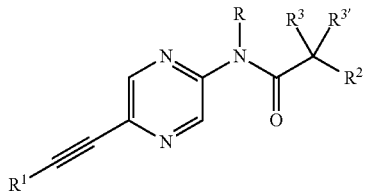

wherein
$R^1$ is phenyl or heteroaryl, which are optionally substituted by halogen, lower alkyl or lower alkoxy;
R is hydrogen or lower alkyl;
$R^2$ is hydrogen, lower alkyl, lower alkoxy, $CF_3$ or S-lower alkyl;
$R^3/R^{3'}$ are independently from each other hydrogen, lower alkyl or lower alkoxy;
or $R^3$ and $R^{3'}$ form together a $C_{3-5}$-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

A further embodiment of the invention are compounds of formula ID

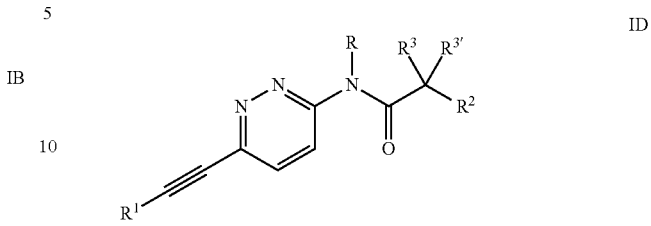

wherein
$R^1$ is phenyl or heteroaryl, which are optionally substituted by halogen, lower alkyl or lower alkoxy;
R is hydrogen or lower alkyl;
$R^2$ is hydrogen, lower alkyl, lower alkoxy, $CF_3$ or S-lower alkyl;
$R^3/R^{3'}$ are independently from each other hydrogen, lower alkyl or lower alkoxy;
or $R^3$ and $R^{3'}$ form together a $C_{3-5}$-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

Examples of compounds of formula ID are the following:
2,2-Dimethyl-N-(6-phenylethynyl-pyridazin-3-yl)-propionamide or
N-[6-(3-Chloro-phenylethynyl)-pyridazin-3-yl]-2,2-dimethyl-propionamide.

A further embodiment of the invention are compounds of formula IE

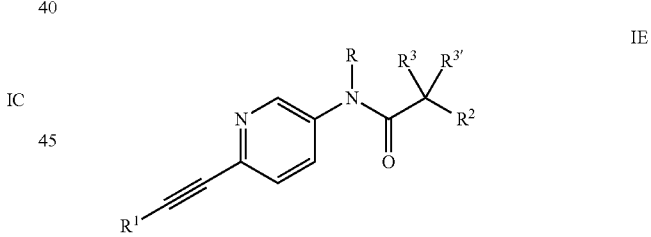

wherein
$R^1$ is phenyl or heteroaryl, which are optionally substituted by halogen, lower alkyl or lower alkoxy;
R is hydrogen or lower alkyl;
$R^2$ is hydrogen, lower alkyl, lower alkoxy, $CF_3$ or S-lower alkyl;
$R^3/R^{3'}$ are independently from each other hydrogen, lower alkyl or lower alkoxy;
or $R^3$ and $R^{3'}$ form together a $C_{3-5}$-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

A further embodiment of the invention are compounds of formula IF

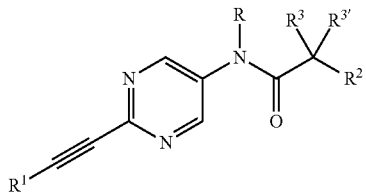

wherein
$R^1$ is phenyl or heteroaryl, which are optionally substituted by halogen, lower alkyl or lower alkoxy;
$R^2$ is hydrogen or lower alkyl;
$R^2$ is hydrogen, lower alkyl, lower alkoxy, $CF_3$ or S-lower alkyl;
$R^3/R^{3'}$ are independently from each other hydrogen, lower alkyl or lower alkoxy;
or $R^3$ and $R^{3'}$ form together a $C_{3-5}$-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

The following definitions of the general terms used in the present description apply irrespective of whether the terms in question appear alone or in combination.

Definitions

As used herein, the term "lower alkyl" denotes a saturated, i.e. aliphatic hydrocarbon group including a straight or branched carbon chain with 1-4 carbon atoms. Examples for "alkyl" are methyl, ethyl, n-propyl, and isopropyl.

The term "alkoxy" denotes a group —O—R' wherein R' is lower alkyl as defined above.

The term "ethynyl" denotes the group —C≡C—.

The term "heteroaryl" denotes a 5 or 6-membered aromatic ring, containing at least one N, O or S-heteroatom, for example pyridinyl, pyrimidinyl, pyrazolyl, pyridazinyl, imidazolyl, triazolyl, thienyl or pyrazinyl.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The preparation of compounds of formula I of the present invention may be carried out in sequential or convergent synthetic routes. Syntheses of the compounds of the invention are shown in the following schemes 1 to 4. The skills required for carrying out the reaction and purification of the resulting products are known to those skilled in the art. The substituents and indices used in the following description of the processes have the significance given herein before.

The compounds of formula I can be manufactured by the methods given below, by the methods given in the examples or by analogous methods. Appropriate reaction conditions for the individual reaction steps are known to a person skilled in the art. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The present compounds of formula I and their pharmaceutically acceptable salts may be prepared by methods, known in the art, for example by the process variant described below, which process comprises a) reacting a compound of formula

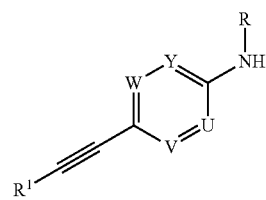

3 with a suitable compound of formula

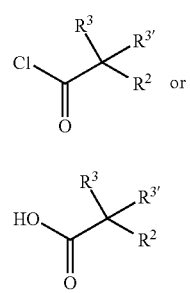

4 or

5 to a compound of formula

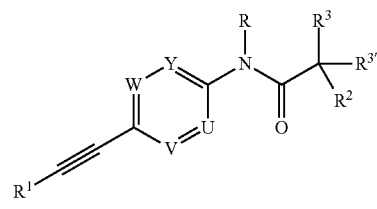

I wherein the substituents are described above, or if desired, converting the compounds obtained into pharmaceutically acceptable acid addition salts, or b) reacting a compound of formula

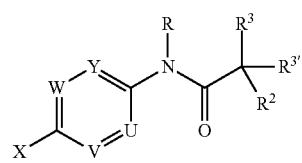

6 with a suitable compound of formula

to a compound of formula

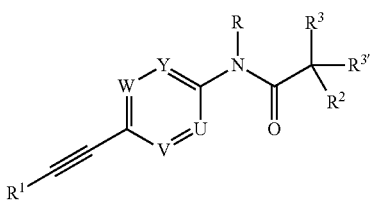

wherein the substituents are described above, or
if desired, converting the compounds obtained into pharmaceutically acceptable acid addition salts, or
c) reacting a compound of formula

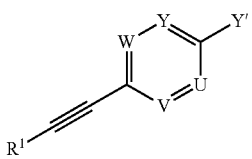

with a suitable compound of formula

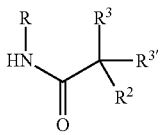

to a compound of formula

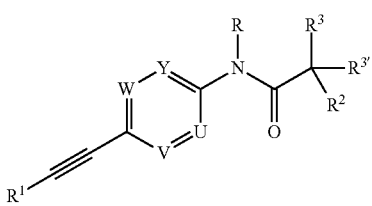

wherein the substituents are described above, or
d) reacting a compound of formula

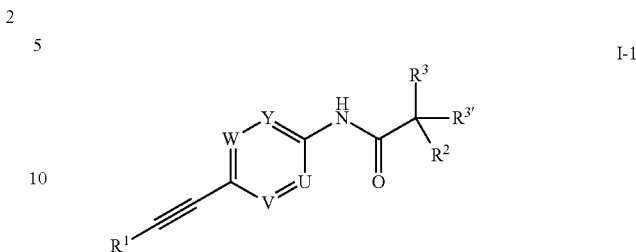

with a suitable compound of formula
to a compound of formula

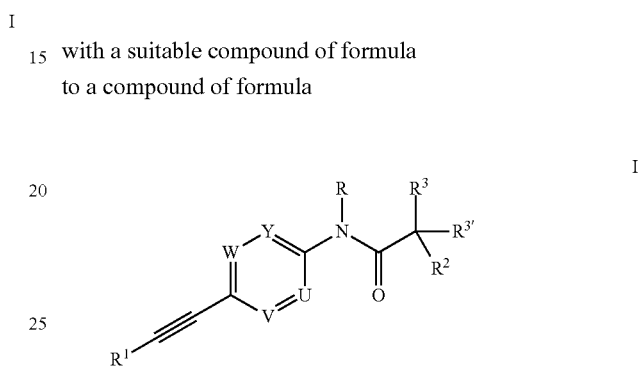

wherein R is halogen and the other substituents are described above, or
if desired, converting the compounds obtained into pharmaceutically acceptable acid addition salts.

The preparation of compounds of formula I is further described in more detail in schemes 1 to 5 and in examples 1-16.

Scheme 1

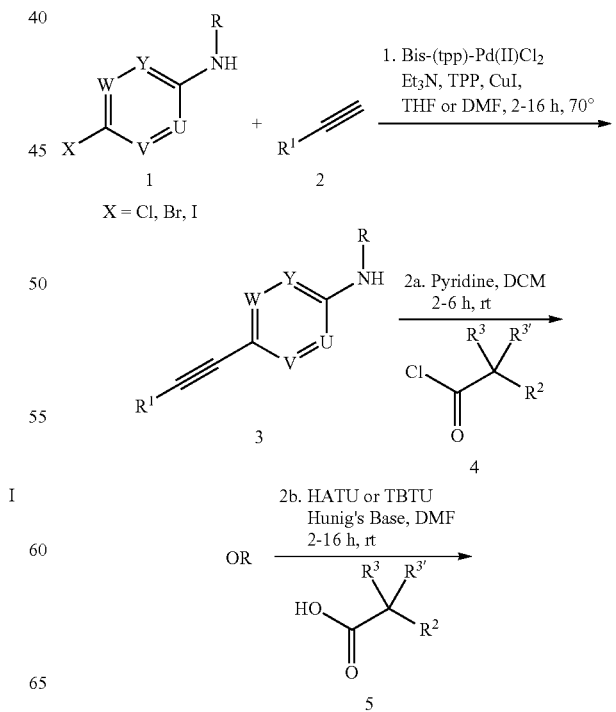

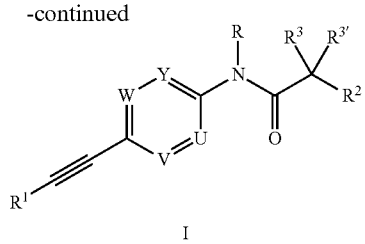

I

An ethynyl compound of formula I can be obtained for example by Sonogashira coupling of an appropriate amine 1 with an appropriately substituted arylacetylene 2 to yield the corresponding ethynyl compound 3. Coupling of ethynyl compound 3 with an appropriately substituted acid chloride 4 with a base such as pyridine in a solvent like dichloromethane or coupling with an appropriately substituted acid 5 with a base such as Hunig's Base and a peptide coupling reagent such as HATU or TBTU in a solvent like DMF yield the desired ethynyl compounds of general formula I. It is also possible to introduce the R substituent at a later time point by alkylation of compounds of formula I, where R=H.

Scheme 2

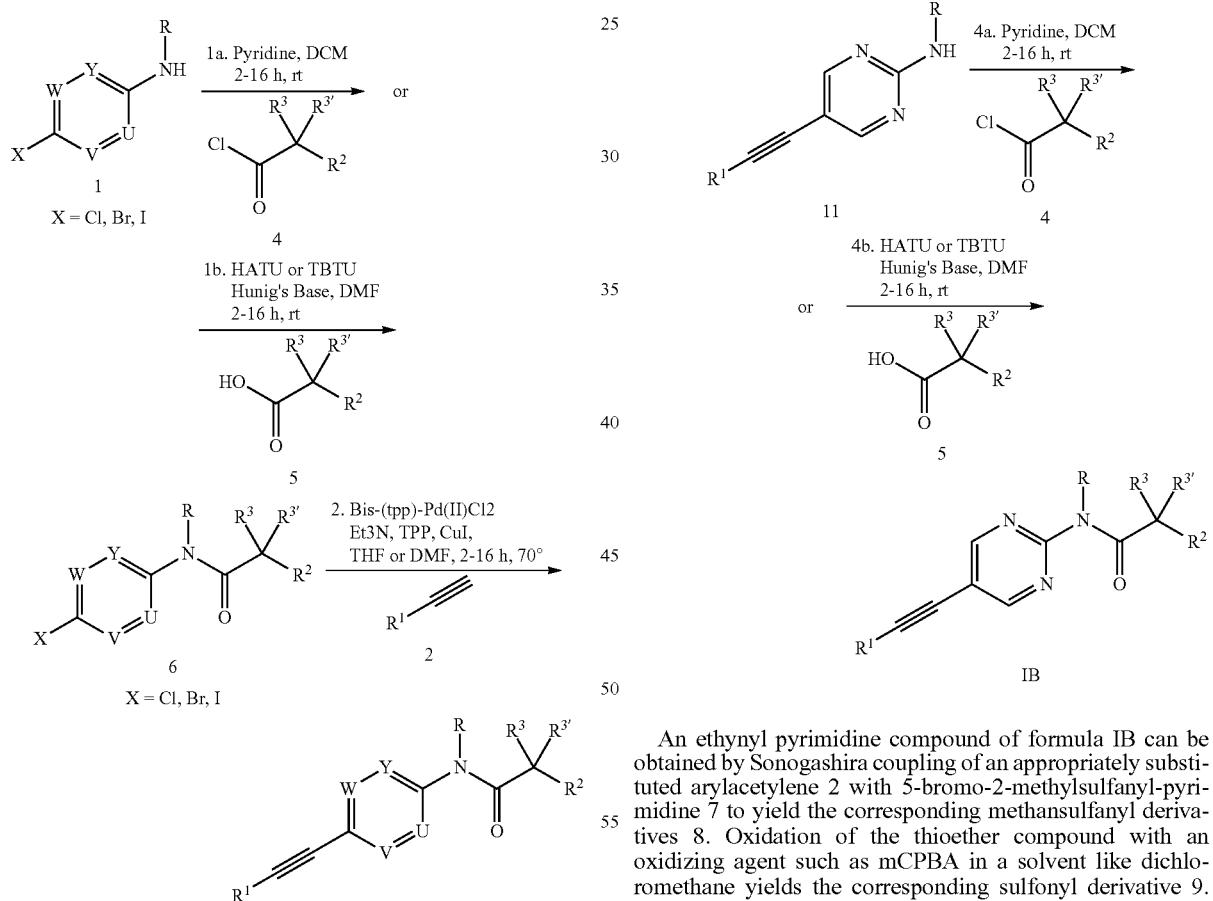

Generally speaking, the sequence of steps used to synthesize the compounds of formula I can also be modified in certain cases, for example by first running the amide coupling to form an appropriately substituted amide derivative 6 followed by Sonogashira coupling with an appropriately substituted arylacetylene 2 using procedures similar to those described in scheme 1. Introduction of the R substituent can also be realized at various points in the synthetic sequence via alkylation of the corresponding intermediate where R=H.

Scheme 3

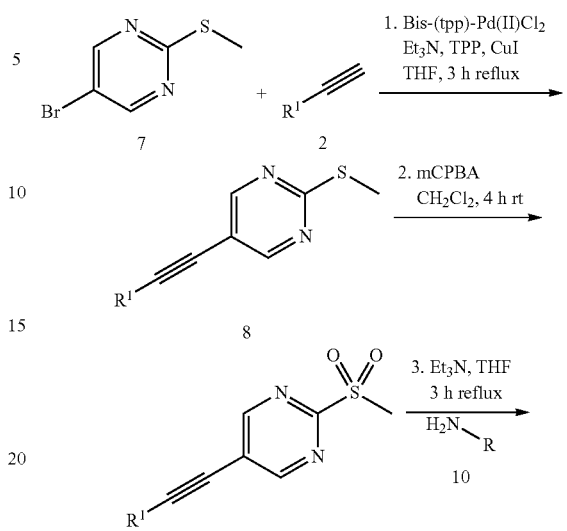

An ethynyl pyrimidine compound of formula IB can be obtained by Sonogashira coupling of an appropriately substituted arylacetylene 2 with 5-bromo-2-methylsulfanyl-pyrimidine 7 to yield the corresponding methansulfanyl derivatives 8. Oxidation of the thioether compound with an oxidizing agent such as mCPBA in a solvent like dichloromethane yields the corresponding sulfonyl derivative 9. Reaction of the sulfonyl derivative with an appropriately substituted amine 10 in the presence of base such as triethylamine in a solvent like THF yields the desired (5-phenylethynyl-pyrimidin-2-yl)-amine 11. Coupling of compound II with an appropriately substituted acid chloride 4 with a base such as pyridine in a solvent like dichloromethane or coupling with an appropriately substituted acid 5 with a base such as Hunig's Base and a peptide coupling reagent such as HATU or TBTU in a solvent like DMF yield the desired ethynyl pyrimidine compounds of general formula IB.

Scheme 4

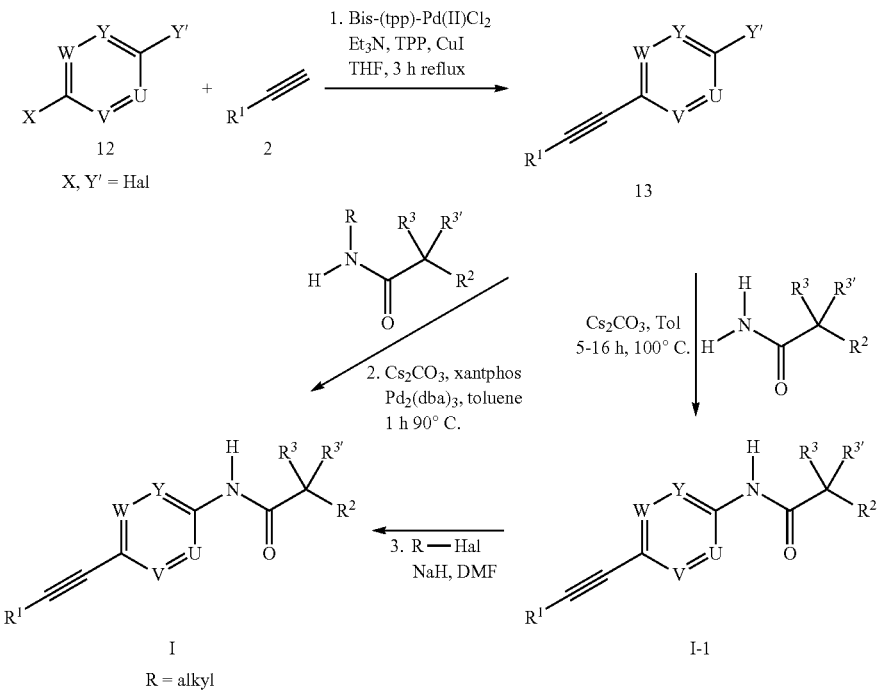

In certain cases it is also possible to selectively react a dihalogenated compound 12 with an acetylene derivative 2 to yield the adduct 13. The amido group can then be directly introduced via a nucleophillic addition (Y'=preferably Cl, F) or a Palladium catalyzed coupling (Buchwald) reaction (Y'=preferably Br or I). The R group can be introduced either directly in the coupling step or via alkylation of compounds of general formula I-1. Of course, depending on X and Y' the sequence of reactions can be inverted by first introducing the amide group followed by the Sonogashira reaction (X=Cl, Br, I preferably Br, I) to introduce the acetylene moiety.

Scheme 5

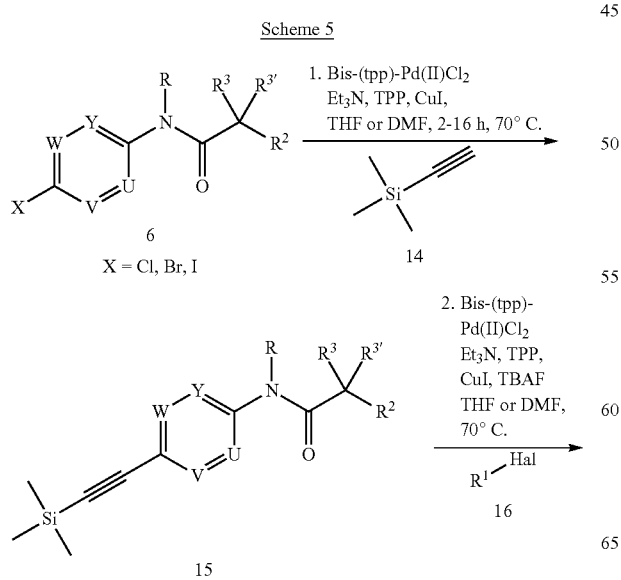

-continued

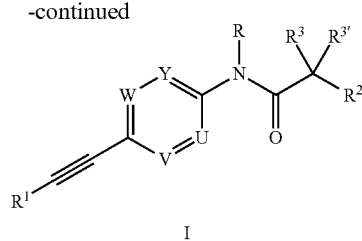

Compounds of formula I can be obtained by Sonogashira coupling of an appropriately substituted amide derivative 6 with ethynyltrimethylsilane 14 to yield the corresponding 5-trimethylsilanylethynyl-derivatives 15. Sonogashira coupling with in-situ desilylation of 15 and an appropriately substituted aryl-halogenide 16 yields the desired compounds of formula I (scheme 5).

EXPERIMENTAL SECTION

Example 1

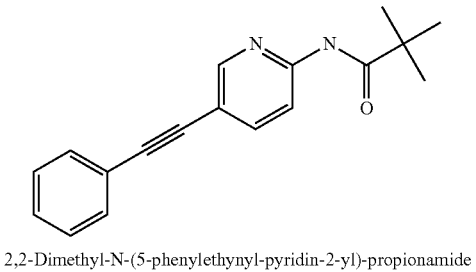 [SMILES: CC(C)(C)C(=O)Nc1ccc(C#Cc2ccccc2)cn1]

2,2-Dimethyl-N-(5-phenylethynyl-pyridin-2-yl)-propionamide

Step 1: 5-Phenylethynyl-pyridin-2-ylamine

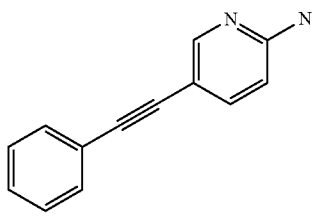 [SMILES: Nc1ccc(C#Cc2ccccc2)cn1]

Bis-(triphenylphosphine)-palladium(II)dichloride (480 mg, 0.68 mmol, 0.05 equiv.) was dissolved in 50 ml THF. (3 g, 13.6 mmol) 2-Amino-5-iodopyridine and phenylacetylene (2.79 g, 27.3 mmol, 2.0 equiv.) were added at room temperature. Triethylamine (5.58 ml, 40.9 mmol, 3 equiv.), triphenylphosphine (111 mg, 0.41 mmol, 0.03 equiv.) and copper (I)iodide (70 mg, 0.41 mmol, 0.03 equiv.) were added and the mixture was stirred for 2 hours at 65° C. The reaction mixture was cooled and extracted with saturated NaHCO$_3$ solution and three times with ethyl acetate. The organic layers were combined, dried over sodium sulfate and evaporated to dryness. The crude product was suspended in dichloromethane, filtered and the solid evaporated to dryness. The desired 5-phenylethynyl-pyridin-2-ylamine (1.6 g, 62% yield) was obtained as a light yellow solid, MS: m/e=195.3 (M+H$^+$).

Step 2: 2,2-Dimethyl-N-(5-phenylethynyl-pyridin-2-yl)-propionamide

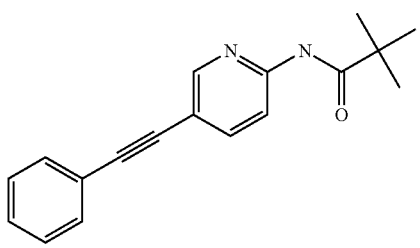 [SMILES: CC(C)(C)C(=O)Nc1ccc(C#Cc2ccccc2)cn1]

(65 mg, 0.33 mmol) 5-Phenylethynyl-pyridin-2-ylamine (Example 1, step 1) was dissolved in dichloromethane (3 ml). Pyridine (52 mg, 53 µl, 0.67 mmol, 2 equiv.) and pivaloyl chloride (48 mg, 50 µl, 0.40 mmol, 1.2 equiv.) were added and the mixture was stirred for 2 hours at room temperature. The reaction mixture was extracted with 1N HCl solution and twice with dichloromethane. The organic extracts were combined, dried over sodium sulfate and evaporated to dryness. The crude product was purified by flash chromatography on a silica gel column eluting with heptane:dichloromethane 50:50. The desired 2,2-dimethyl-N-(5-phenylethynyl-pyridin-2-yl)-propionamide (40 mg, 43% yield) was obtained as a light yellow solid, MS: m/e=279.3 (M+H$^+$).

Example 2

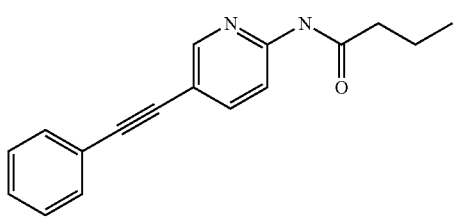

N-(5-Phenylethynyl-pyridin-2-yl)-butyramide

The title compound was obtained as a white solid, MS: m/e=265.3 (M+H$^+$), using chemistry similar to that described in Example 1, step 2 from 5-phenylethynyl-pyridin-2-ylamine (Example 1, step 1) and butyryl chloride.

Example 3

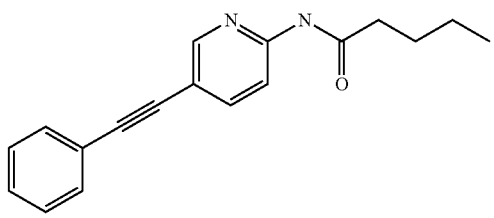

Pentanoic acid (5-phenylethynyl-pyridin-2-yl)-amide

The title compound was obtained as a white solid, MS: m/e=279.3 (M+H$^+$), using chemistry similar to that described in Example 1, step 2 from 5-phenylethynyl-pyridin-2-ylamine (Example 1, step 1) and valeryl chloride.

Example 4

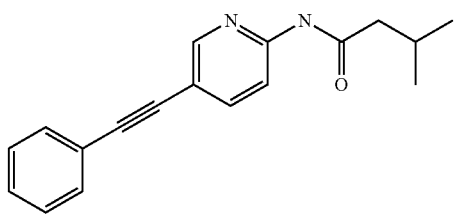

3-Methyl-N-(5-phenylethynyl-pyridin-2-yl)-butyramide

The title compound was obtained as a white solid, MS: m/e=279.3 (M+H$^+$), using chemistry similar to that described in Example 1, step 2 from 5-phenylethynyl-pyridin-2-ylamine (Example 1, step 1) and isovaleroyl chloride.

Example 5

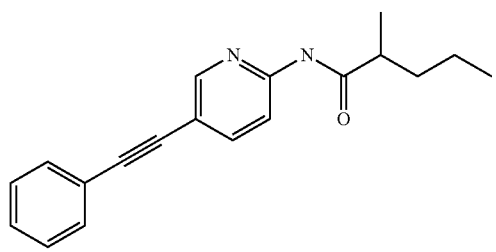

(RS)-2-Methyl-pentanoic acid (5-phenylethynyl-pyridin-2-yl)-amide

The title compound was obtained as a white solid, MS: m/e=293.3 (M+H$^+$), using chemistry similar to that described in Example 1, step 2 from 5-phenylethynyl-pyridin-2-ylamine (Example 1, step 1) and (RS)-2-methylvaleroyl chloride.

Example 6

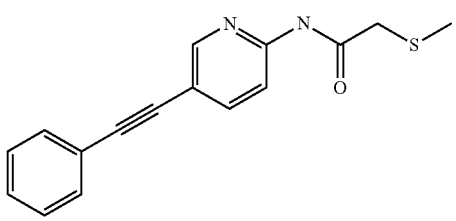

2-Methylsulfanyl-N-(5-phenylethynyl-pyridin-2-yl)-acetamide

Step 1: N-(5-Bromo-pyridin-2-yl)-2-methylsulfanyl-acetamide

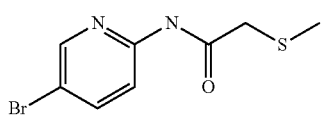

(1 g, 5.78 mmol) 5-Bromopyridin-2-amine was dissolved in DMF (40 ml) and HATU (2.64 g, 6.94 mmol, 1.2 equiv.) was added. After 15 minutes at room temperature Hunig's Base (6.0 ml, 34.7 mmol, 6 equiv.) and 2-(methylthio)acetic acid (736 mg, 6.94 mmol, 1.2 equiv.) were added. The mixture was stirred for 72 hours at room temperature. The reaction mixture was evaporated and extracted three times with saturated $Na_2CO_3$ solution and three times with ethyl acetate. The organic layers were extracted three times with 1N HCl solution and evaporated to dryness. The crude product was suspended in pentane, filtered and the solid evaporated to dryness. The desired N-(5-bromo-pyridin-2-yl)-2-methylsulfanyl-acetamide (312 mg, 21% yield) was obtained as a yellow solid, MS: m/e=258.9/260.8 (M+H⁺).

Step 2: 2-Methylsulfanyl-N-(5-phenylethynyl-pyridin-2-yl)-acetamide

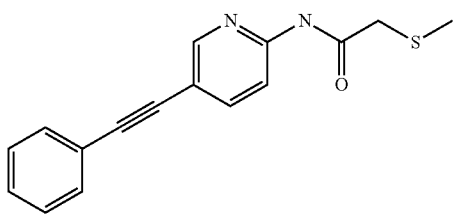

The title compound was obtained as a white solid, MS: m/e=283.1 (M+H⁺), using chemistry similar to that described in Example 1, step 1 from N-(5-bromo-pyridin-2-yl)-2-methylsulfanyl-acetamide (Example 6, step 1) and phenylacetylene.

Example 7

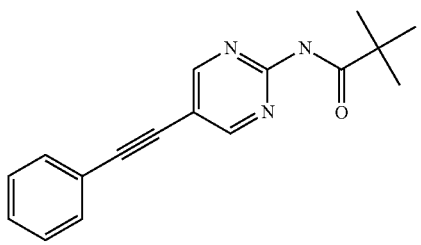

2,2-Dimethyl-N-(5-phenylethynyl-pyrimidin-2-yl)-propionamide

Step 1: N-(5-Bromo-pyrimidin-2-yl)-2,2-dimethyl-propionamide

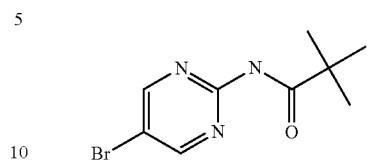

The title compound was obtained as a white solid, MS: m/e=258.0/259.9 (M+H⁺), using chemistry similar to that described in Example 1, step 2 from 2-amino-5-bromopyrimidine and pivaloyl chloride.

Step 2: 2,2-Dimethyl-N-(5-phenylethynyl-pyrimidin-2-yl)-propionamide

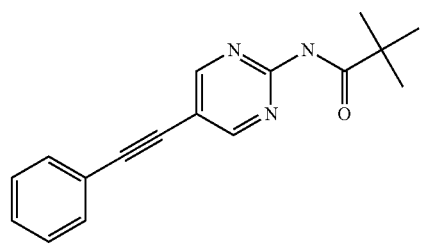 [SMILES: CC(C)(C)C(=O)Nc1ncc(C#Cc2ccccc2)cn1]

The title compound was obtained as a light yellow solid, MS: m/e=280.1 (M+H⁺), using chemistry similar to that described in Example 1, step 1 from N-(5-bromo-pyrimidin-2-yl)-2,2-dimethyl-propionamide (Example 7, step 1) and phenylacetylene.

Example 8

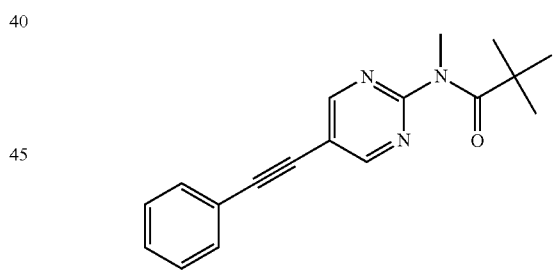

2-2,N-Trimethyl-N-(5-phenylethynyl-pyrimidin-2-yl)-priopionamide

Step 1:
2-Methylsulfanyl-5-phenylethynyl-pyrimidine

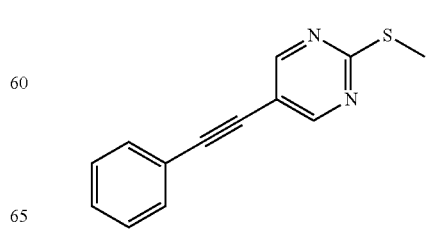

Bis-(triphenylphosphine)-palladium(II)dichloride (120 mg, 0.16 mmol, 0.05 equiv.) were dissolved in 50 ml THF and 5-bromo-2-methylsulfanyl-pyrimidine (840 mg, 4.1 mmol) and phenylacetylene (410 µl, 4.1 mmol, 1 equiv.) were added at room temperature. Triethylamine (1.36 ml, 12.3 mmol, 3 equiv.), triphenylphosphine (28 mg, 0.12 mmol, 0.03 equiv.) and copper(I)iodide (19 mg, 0.08 mmol, 0.03 equiv.) were added and the mixture was stirred for 3 hours at 65° C. The reaction mixture was cooled and extracted once with saturated NaHCO$_3$ solution and three times with ethyl acetate. The organic layers were combined, dried with sodium sulfate, filtered and evaporated to dryness. The crude product was purified by flash chromatography on silicagel (heptane:ethyl acetate 100:0->50:50). The desired 2-Methylsulfanyl-5-phenylethynyl-pyrimidine was obtained as a light yellow solid (400 mg, 44%), MS: m/e=227.3 (M+H$^+$).

Step 2:
2-Methanesulfonyl-5-phenylethynyl-pyrimidine

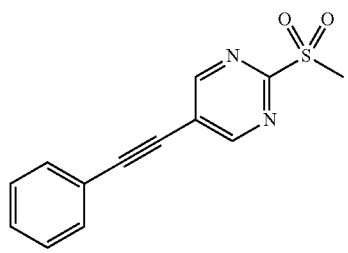 [SMILES: CS(=O)(=O)c1ncc(C#Cc2ccccc2)cn1]

(360 mg, 1.60 mmol) 2-Methylsulfanyl-5-phenylethynyl-pyrimidine (Example 8, step 1) was dissolved in 20 ml of dichloromethane and 3-chloroperbenzoic acid (870 mg, 3.50 mmol, 2.2 equiv.) was added in several portions at 0-5° C. The reaction mixture was stirred for 4 hours at room temperature. Saturated NaHCO$_3$ solution was added and the mixture was extracted three times with ethyl acetate. The organic extracts were dried with sodium sulfate, filtered and evaporated. The crude product was purified by flash chromatography on silicagel (dichloromethane). The desired 2-methanesulfonyl-5-phenylethynyl-pyrimidine was obtained as a white solid (400 mg, 97%), MS: m/e=259.2 (M+H$^+$).

Step 3:
Methyl-(5-phenylethynyl-pyrimidin-2-yl)-amine

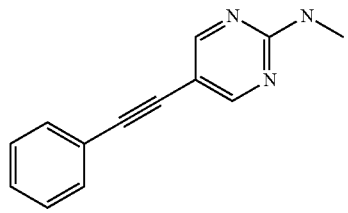 [SMILES: CNc1ncc(C#Cc2ccccc2)cn1]

(100 mg, 0.38 mmol) 2-Methanesulfonyl-5-phenylethynyl-pyrimidine (Example 8, step 2), methylamine hydrochloride (52 mg, 0.77 mmol, 2 equiv.) and Et$_3$N (220 µl, 1.55 mmol, 4 equiv.) were suspended in 1 ml THF and stirred for 1 hour at 65° C. The reaction mixture was concentrated in vacuo and the residue was purified by flash chromatography by directly loading the crude material onto a silica gel column and eluting with (heptane:ethyl acetate 100:0->0:100). The desired methyl-(5-phenylethynyl-pyrimidin-2-yl)-amine was obtained as a white solid (38 mg, 47%), MS: m/e=210.2 (M+H$^+$).

Step 4: 2,2,N-Trimethyl-N-(5-phenylethynyl-pyrimidin-2-yl)-propionamide

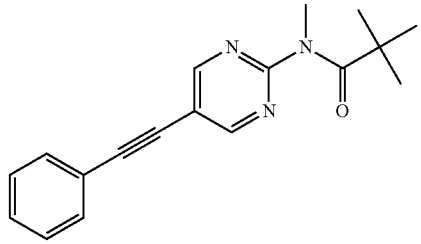 [SMILES: CN(C(=O)C(C)(C)C)c1ncc(C#Cc2ccccc2)cn1]

The title compound was obtained as a white solid, MS: m/e=294.0 (M+H$^+$), using chemistry similar to that described in Example 1, step 2 from methyl-(5-phenylethynyl-pyrimidin-2-yl)-amine (Example 8, step 3) and pivaloyl chloride.

Example 9

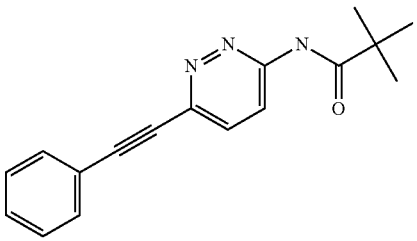

2,2-Dimethyl-N-(6-phenylethynyl-pyridazin-3-yl)-propionamide

To a suspension of 3-chloro-6-(phenyl ethynyl)pyridazine (CAS 77778-15-5) (200 mg, 0.93 mmol) and pivalamide (113 mg, 1.12 mmol, 1.2 equiv.) in 4 ml of toluene were added cesium carbonate (364 mg, 1.12 mmol, 1.2 equiv.). The suspension was heated for 20 hours at 120° C. and then allowed to cool to room temperature. Ethyl acetate (10 ml) was added and the unsoluble salts were filtered off. After concentration in vacuum, the residue was purified by flash chromatography eluting with heptane followed by a heptane to 60% ethyl acetate/heptane gradient to yield 19 mg (7%) of the title compound as a light yellow solid, MS: m/e=280.2 (M+H+).

Example 10

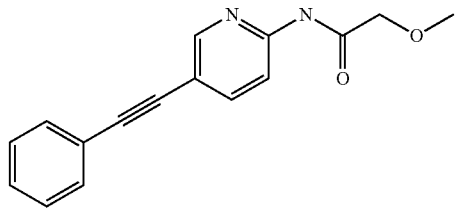

2-Methoxy-N-(5-phenylethynyl-pyridin-2-yl)-acetamide

The title compound was obtained as a white solid, MS: m/e=267.0 (M+H$^+$), using chemistry similar to that described in Example 1, step 2 from 5-phenylethynyl-pyridin-2-ylamine (Example 1, step 1) and 2-methoxyacetyl chloride.

Example 11

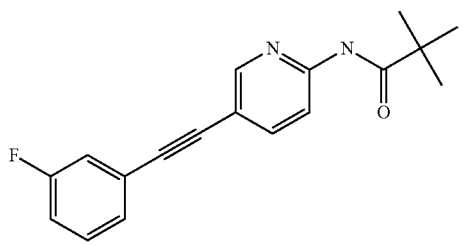 [SMILES: CC(C)(C)C(=O)Nc1ccc(C#Cc2cccc(F)c2)cn1]

N-[5-(3-Fluoro-phenylethynyl)-pyridin-2-yl]-2,2-dimethyl-propionamide

Step 1:
N-(5-Bromo-pyridin-2-yl-2,2-dimethyl-propionamide

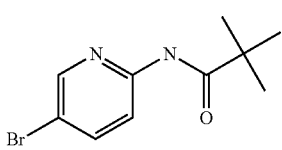

The title compound was obtained as a colorless oil, MS: m/e=257.1/259.0 (M+H$^+$), using chemistry similar to that described in Example 1, step 2 from 2-amino-5-bromopyridine and pivaloyl chloride.

Step 2: N-[5-(3-Fluoro-phenylethynyl-pyridin-2-yl]-2,2-dimethyl-propionamide

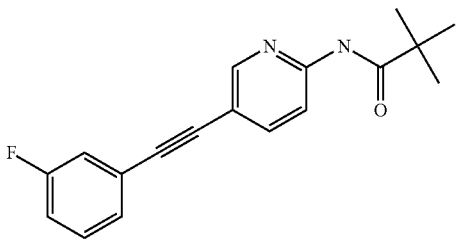

The title compound was obtained as a yellow solid, MS: m/e=297.2 (M+H$^+$), using chemistry similar to that described in Example 1, step 1 from N-(5-bromo-pyridin-2-yl)-2,2-dimethyl-propionamide (Example 11, step 1) and 3-fluorophenylacetylene.

Example 12

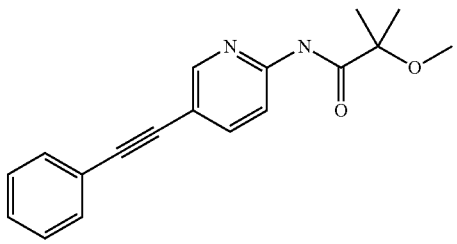

2-Methoxy-2-methyl-N-(5-phenylethynyl-pyridin-2-yl)-propionamide (100 mg, 0.515 mmol) 5-Phenylethynyl-pyridin-2-ylamine (Example 1, step 1) was dissolved in dichloromethane (5 ml) and 2-methoxy-2-methylpropionic acid (91 mg, 0.77 mmol, 1.5 equiv.), 2-bromo-1-ethyl pyridinium tetrafluoroborate (CAS 878-23-9) (211 mg, 0.77 mmol, 1.5 equiv.) and Hunig's Base (0.26 ml, 1.54 mmol, 3 equiv.) were added. The mixture was stirred for 14 hours at room temperature. The reaction mixture was extracted with saturated Na$_2$CO$_3$ solution and dichloromethane. The organic layer was dried over sodium sulfate and evaporated to dryness. The crude product was purified by prep HPLC to afford the desired 2-methoxy-2-methyl-N-(5-phenylethynyl-pyridin-2-yl)-propionamide (70 mg, 46% yield) was obtained as a yellow oil, MS: m/e=295.2 (M+H$^+$).

Example 13

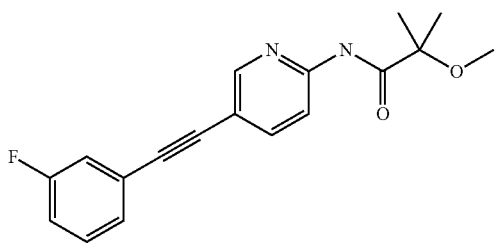

N-[5-(3-Fluoro-phenylethynyl)-pyridin-2-yl]-2-methoxy-2-methyl-propionamide

Step 1: N (5-Iodo-pyridin-2-yl)-2-methoxy-2-methyl-propionamide

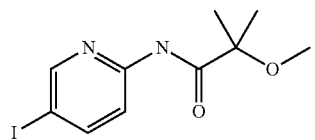

The title compound was obtained as a colorless oil using chemistry similar to that described in Example 12 from 2-amino-5-iodopyridine and 2-methoxy-2-methylpropionic acid.

Step 2: 2-Methoxy-2-methyl-N-(5-trimethylsilanyl-ethynyl-pyridin-2-yl)-propionamide

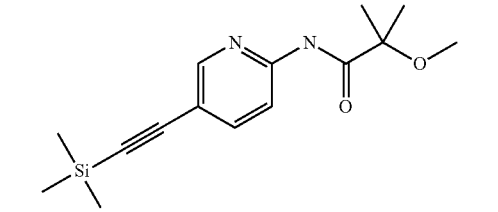

The title compound was obtained as a yellow oil, MS: m/e=290.8 (M+H$^+$), using chemistry similar to that described in Example 1, step 1 from N-(5-iodo-pyridin-2-yl)-2-methoxy-2-methyl-propionamide (Example 13, step 1) and trimethylsilylacetylene.

Step 3: N-[5-(3-Fluoro-phenylethynyl-pyridin-2-yl]-2-methoxy-2-methyl-propionamide

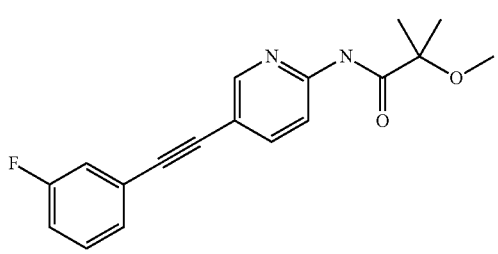 [SMILES: COC(C)(C)C(=O)Nc1ccc(C#Cc2cccc(F)c2)cn1]

2-Methoxy-2-methyl-N-(5-trimethylsilanylethynyl-pyridin-2-yl)-propionamide (Example 13, step 2) (90 mg, 0.31 mmol) was dissolved in THF (8 ml). 1-Fluoro-3-iodobenzene (83 mg, 0.37 mmol, 1.2 equiv.), Et$_3$N (130 µl, 0.93 mmol, 3 equiv.), bis-(triphenylphosphine)-palladium(II)dichloride (11 mg, 15 µmol, 0.05 equiv.) and copper(I)iodide (1.8 mg, 10 µmol, 0.03 equiv.) were added under nitrogen and the mixture was heated to 70° C. TBAF 1M in THF (370 µl, 0.37 mmol, 1.2 equiv.) was added dropwise at 70° C. The reaction mixture was stirred for 1 hour at 70° C., filtered through celite and the filtrate evaporated to dryness. The crude product was purified by flash chromatography with a silica gel column eluting with heptane:ethyl acetate 100:0->90:10. The desired N-[5-(3-fluoro-phenylethynyl)-pyridin-2-yl]-2-methoxy-2-methyl-propionamide (64 mg, 66% yield) was obtained as a yellow oil, MS: m/e=313.0 (M+H$^+$).

Example 14

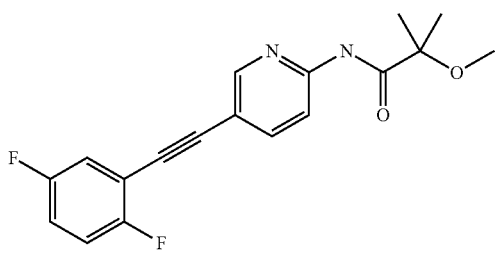

N-[5-(2,5-Difluoro-phenylethynyl)-pyridin-2-yl]-2-methoxy-2-methyl-propionamide

The title compound was obtained as a white solid, MS: m/e=331.0 (M+H$^+$), using chemistry similar to that described in Example 13, step 3 from 2-methoxy-2-methyl-N-(5-trimethylsilanylethynyl-pyridin-2-yl)-propionamide (Example 13, step 2) and 1,4-difluoro-2-iodobenzene.

Example 15

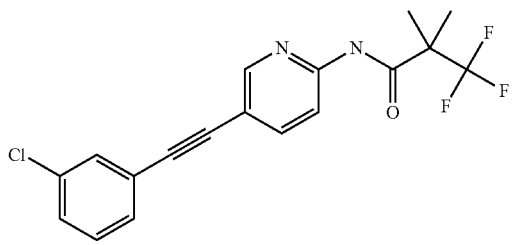 [SMILES: CC(C)(C(=O)Nc1ccc(C#Cc2cccc(Cl)c2)cn1)C(F)(F)F]

N-[5-(3-Chloro-phenylethynyl)-pyridin-2-yl]-3,3,3-trifluoro-2,2-dimethyl-propionamide Step 1: 3,3,3-Trifluoro-N-5-iodo-pyridin-2-yl)-2,2-dimethyl-propionamide

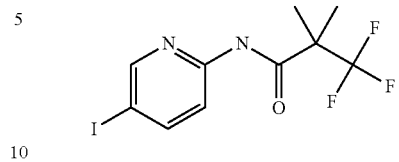

The title compound was obtained as a yellow oil: m/e=359.4 (M+H$^+$), using chemistry similar to that described in Example 12 from 2-amino-5-iodopyridine and 3,3,3-trifluoro-2,2-dimethylpropanoic acid.

Step 2: N-[5-(3-Chloro-phenylethynyl)-pyridin-2-yl]-3,3,3-trifluoro-2,2-dimethyl-propionamide

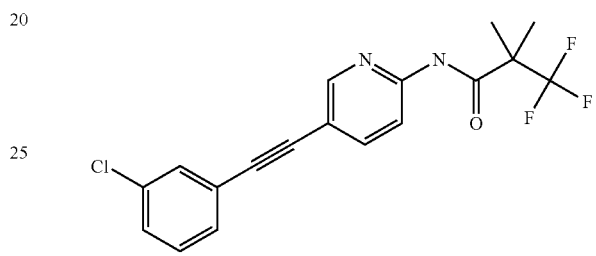

The title compound was obtained as a light yellow oil, MS: m/e=365.5/367.5 (M+H$^+$), using chemistry similar to that described in Example 1, step 1 from 3,3,3-trifluoro-N-(5-iodo-pyridin-2-yl)-2,2-dimethyl-propionamide (Example 15, step 1) and 3-chlorophenylacetylene.

Example 16

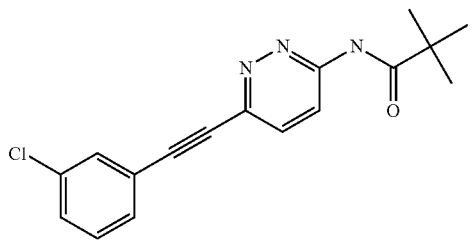 [SMILES: CC(C)(C)C(=O)Nc1ccc(C#Cc2cccc(Cl)c2)nn1]

N-[6-(3-Chloro-phenylethynyl)-pyridazin-3-yl]-2,2-dimethyl-propionamide

Step 1: N-(6-Chloro-pyridazin-3-yl)-2,2-dimethyl-propionamide

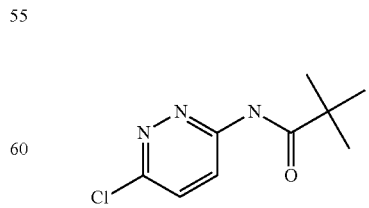

The title compound was obtained as a white solid, MS: m/e=214.2/216.2 (M+H$^+$), using chemistry similar to that described in Example 1, step 2 from 3-amino-6-chloropyridazine and pivaloyl chloride.

Step 2: N-[6-(3-Chloro-phenylethynyl)-pyridazin-3-yl]-2,2-dimethyl-propionamide

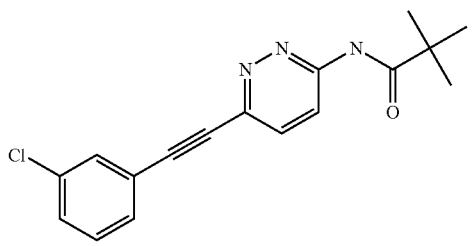

The title compound was obtained as a light yellow solid, MS: m/e=314.5/316.5 (M+H$^+$), using chemistry similar to that described in Example 1, step 1 from N-(6-chloro-pyridazin-3-yl)-2,2-dimethyl-propionamide (Example 16, step 1) and 3-chlorophenylacetylene.

Biological Assay and Data

Intracellular Ca$^{2+}$ Mobilization Assay

A monoclonal HEK-293 cell line stably transfected with a cDNA encoding for the human mGlu5a receptor was generated; for the work with mGlu5 Positive Allosteric Modulators (PAMs), a cell line with low receptor expression levels and low constitutive receptor activity was selected to allow the differentiation of agonistic versus PAM activity. Cells were cultured according to standard protocols (Freshney, 2000) in Dulbecco's Modified Eagle Medium with high glucose supplemented with 1 mM glutamine, 10% (vol/vol) heat-inactivated bovine calf serum, Penicillin/Streptomycin, 50 μg/ml hygromycin and 15 μg/ml blasticidin (all cell culture reagents and antibiotics from Invitrogen, Basel, Switzerland).

About 24 hrs before an experiment, 5×10$^4$ cells/well were seeded in poly-D-lysine coated, black/clear-bottomed 96-well plates. The cells were loaded with 2.5 μM Fluo-4AM in loading buffer (1×HBSS, 20 mM HEPES) for 1 hr at 37° C. and washed five times with loading buffer. The cells were transferred into a Functional Drug Screening System 7000 (Hamamatsu, Paris, France), and 11 half logarithmic serial dilutions of test compound at 37° C. were added and the cells were incubated for 10-30 min. with on-line recording of fluorescence. Following this pre-incubation step, the agonist L-glutamate was added to the cells at a concentration corresponding to EC$_{20}$ (typically around 80 μM) with on-line recording of fluorescence; in order to account for day-to-day variations in the responsiveness of cells, the EC$_{20}$ of glutamate was determined immediately ahead of each experiment by recording of a full dose-response curve of glutamate.

Responses were measured as peak increase in fluorescence minus basal (i.e. fluorescence without addition of L-glutamate), normalized to the maximal stimulatory effect obtained with saturating concentrations of L-glutamate. Graphs were plotted with the % maximal stimulatory using XLfit, a curve fitting program that iteratively plots the data using Levenburg Marquardt algorithm. The single site competition analysis equation used was y=A+((B−A)/(1+((x/C)D))), where y is the % maximal stimulatory effect, A is the minimum y, B is the maximum y, C is the EC$_{50}$, x is the log 10 of the concentration of the competing compound and D is the slope of the curve (the Hill Coefficient). From these curves the EC$_{50}$ (concentration at which half maximal stimulation was achieved), the Hill coefficient as well as the maximal response in % of the maximal stimulatory effect obtained with saturating concentrations of L-glutamate were calculated.

Positive signals obtained during the pre-incubation with the PAM test compounds (i.e. before application of an EC$_{20}$ concentration of L-glutamate) were indicative of an agonistic activity, the absence of such signals were demonstrating the lack of agonistic activities. A depression of the signal observed after addition of the EC$_{20}$ concentration of L-glutamate was indicative of an inhibitory activity of the test compound.

In the list of examples below are shown the corresponding results for compounds which all have EC$_{50}$<100 nM.

List of Examples

| Ex. | Structure | Name | EC$_{50}$ (nM) mGlu5PAM | Eff. (%) |
|---|---|---|---|---|
| 1 | 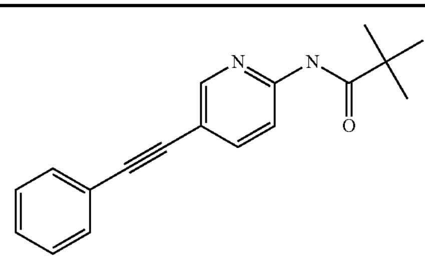 | 2,2-Dimethyl-N-(5-phenylethynyl-pyridin-2-yl)-propionamide | 19 | 72 |
| 2 | 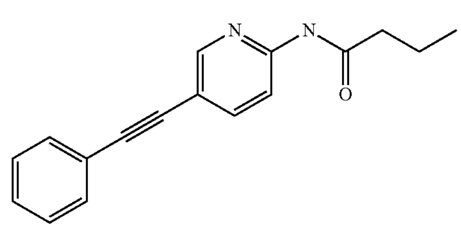 [SMILES: CCCC(=O)Nc1ccc(C#Cc2ccccc2)cn1] | N-(5-Phenylethynyl-pyridin-2-yl)-butyramide | 70 | 52 |

-continued

| Ex. | Structure | Name | EC$_{50}$ (nM) mGlu5PAM | Eff. (%) |
|---|---|---|---|---|
| 3 | 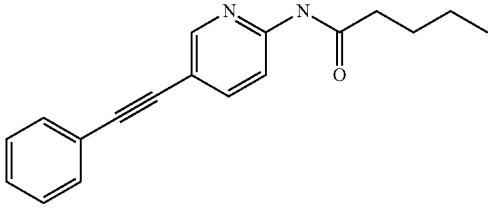 | Pentanoic acid (5-phenylethynyl-pyridin-2-yl)-amide | 48 | 84 |
| 4 | 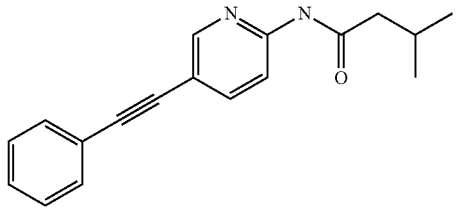 [SMILES: CC(C)CC(=O)Nc1ccc(C#Cc2ccccc2)cn1] | 3-Methyl-N-(5-phenylethynyl-pyridin-2-yl)-butyramide | 71 | 83 |
| 5 | 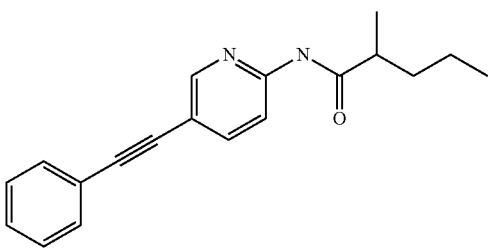 | (RS)-2-Methyl-pentanoic acid (5-phenylethynyl-pyridin-2-yl)-amide | 48 | 75 |
| 6 | 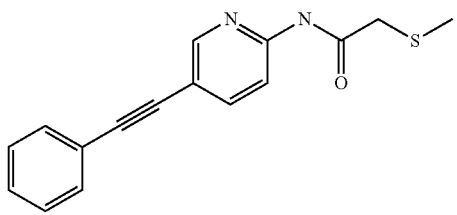 | 2-Methylsulfanyl-N-(5-phenylethynyl-pyridin-2-yl)-acetamide | 18 | 47 |
| 7 | 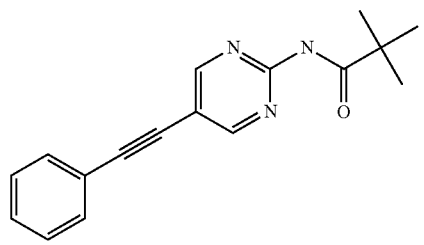 [SMILES: CC(C)(C)C(=O)Nc1ncc(C#Cc2ccccc2)cn1] | 2,2-Dimethyl-N-(5-phenylethynyl-pyrimidin-2-yl)-propionamide | 56 | 59 |
| 8 | 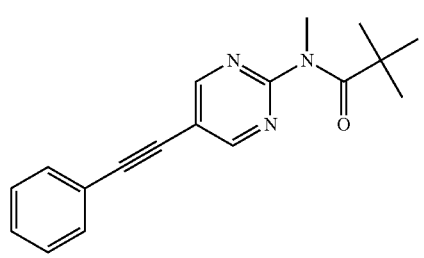 [SMILES: CN(C(=O)C(C)(C)C)c1ncc(C#Cc2ccccc2)cn1] | 2,2,N-Trimethyl-N-(5-phenylethynyl-pyrimidin-2-yl)-propionamide | 52 | 74 |

-continued

| Ex. | Structure | Name | EC$_{50}$ (nM) mGlu5PAM | Eff. (%) |
|---|---|---|---|---|
| 9 | 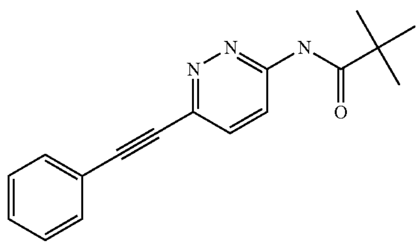 [SMILES: CC(C)(C)C(=O)Nc1ccc(C#Cc2ccccc2)nn1] | 2,2-Dimethyl-N-(6-phenylethynyl-pyridazin-3-yl)-propionamide | 6 | 73 |
| 10 | 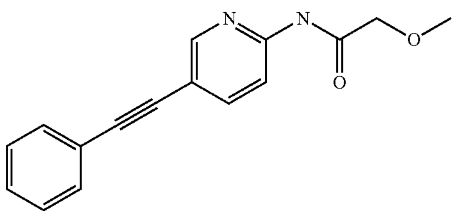 | 2-Methoxy-N-(5-phenylethynyl-pyridin-2-yl)-acetamide | 49 | 43 |
| 11 | 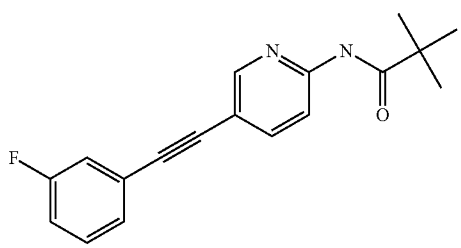 [SMILES: CC(C)(C)C(=O)Nc1ccc(C#Cc2cccc(F)c2)cn1] | N-[5-(3-Fluoro-phenylethynyl)-pyridin-2-yl]-2,2-dimethyl-propionamide | 15 | 44 |
| 12 | 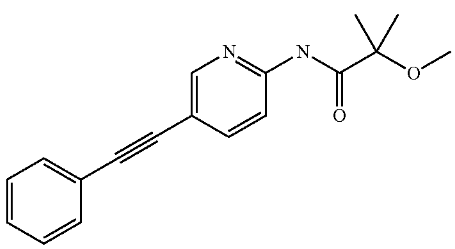 [SMILES: COC(C)(C)C(=O)Nc1ccc(C#Cc2ccccc2)cn1] | 2-Methoxy-2-methyl-N-(5-phenylethynyl)-pyridin-2-yl)-propionamide | 77 | 68 |
| 13 | 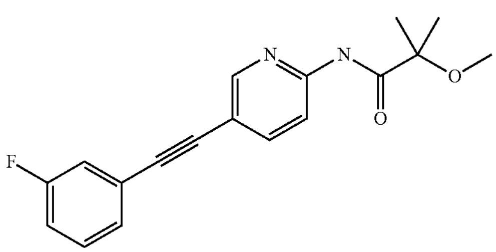 [SMILES: COC(C)(C)C(=O)Nc1ccc(C#Cc2cccc(F)c2)cn1] | N-[5-(3-Fluoro-phenylethynyl)-pyridin-2-yl]-2-methoxy-2-methyl-propionamide | 85 | 54 |
| 14 | 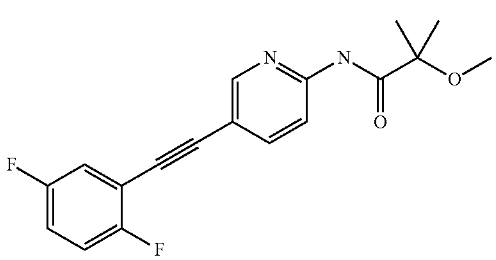 [SMILES: COC(C)(C)C(=O)Nc1ccc(C#Cc2cc(F)ccc2F)cn1] | N-[5-(2,5-Difluoro-phenylethynyl)-pyridin-2-yl]-2-methoxy-2-methyl-propionamide | 94 | 47 |

| Ex. | Structure | Name | EC$_{50}$ (nM) mGlu5PAM | Eff. (%) |
|---|---|---|---|---|
| 15 | 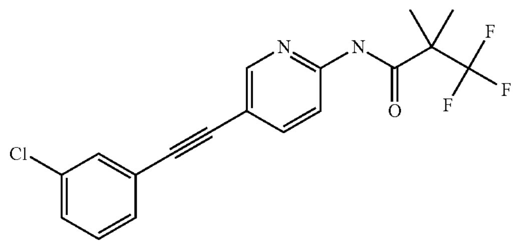 [SMILES: CC(C)(C(=O)Nc1ccc(C#Cc2cccc(Cl)c2)cn1)C(F)(F)F] | N-[5-(3-Chloro-phenylethynyl)-pyridin-2-yl]-3,3,3-trifluoro-2,2-dimethyl-propionamide | 19 | 46 |
| 16 | 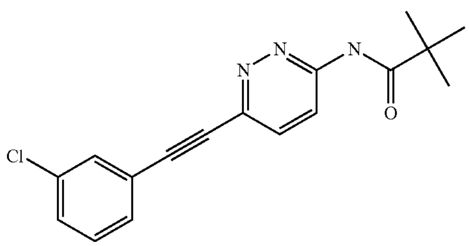 [SMILES: CC(C)(C)C(=O)Nc1ccc(C#Cc2cccc(Cl)c2)nn1] | N-[6-(3-Chloro-phenylethynyl)-pyridazin-3-yl]-2,2-dimethyl-propionamide | 7 | 45 |

The compounds of formula (I) and pharmaceutically acceptable salts thereof can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. However, the administration can also be effected rectally, e.g. in the form of suppositories, or parenterally, e.g. in the form of injection solutions.

The compounds of formula (I) and pharmaceutically acceptable salts thereof can be processed with pharmaceutically inert, inorganic or organic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of formula (I), but as a rule are not necessary. Suitable carriers for suppositories are, for example, natural or hardened oils, waxes, fats, semi-liquid or liquid polyols and the like.

In addition, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

As mentioned earlier, medicaments containing a compound of formula (I) or pharmaceutically acceptable salts thereof and a therapeutically inert excipient are also an object of the present invention, as is a process for the production of such medicaments which comprises bringing one or more compounds of formula I or pharmaceutically acceptable salts thereof and, if desired, one or more other therapeutically valuable substances into a galenical dosage form together with one or more therapeutically inert carriers.

As further mentioned earlier, the use of the compounds of formula (I) for the preparation of medicaments useful in the prevention and/or the treatment of the above recited diseases is also an object of the present invention.

The dosage can vary within wide limits and will, of course, be fitted to the individual requirements in each particular case. In general, the effective dosage for oral or parenteral administration is between 0.01-20 mg/kg/day, with a dosage of 0.1-10 mg/kg/day being preferred for all of the indications described. The daily dosage for an adult human being weighing 70 kg accordingly lies between 0.7-1400 mg per day, preferably between 7 and 700 mg per day.

Pharmaceutical Compositions Comprising Compounds of the Invention:

Tablets of the following composition are produced in a conventional manner:

| | mg/Tablet |
|---|---|
| Active ingredient | 100 |
| Powdered. lactose | 95 |
| White corn starch | 35 |
| Polyvinylpyrrolidone | 8 |
| Na carboxymethylstarch | 10 |
| Magnesium stearate | 2 |
| Tablet weight | 250 |

What is claimed:

1. A compound of formula I

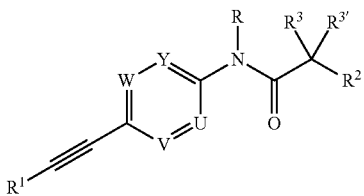

wherein
Y is N or CH; with the proviso that Y can only be CH, if at least one of U, V or W are N;
U is N or C—R⁴;
V and W are independently N or CH;
 with the proviso that only one of U, V or W can be simultaneously nitrogen;
$R^4$ is hydrogen, methyl or halogen;
$R^1$ is phenyl or heteroaryl, which are optionally substituted by halogen, lower alkyl or lower alkoxy;
R is hydrogen or lower alkyl;
$R^2$ is hydrogen, lower alkyl, lower alkoxy, $CF_3$ or S-lower alkyl;
$R^3/R^{3'}$ are, independently from each other, hydrogen, lower alkyl or lower alkoxy;
 or $R^3$ and $R^{3'}$ form together a $C_{3-5}$-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

2. The compound of claim 1 having the formula

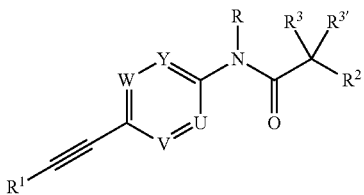

wherein
Y is N;
U is —CH— or N;
V and W are independently N or CH;
 with the proviso that only one of U, V or W can be simultaneously nitrogen;
$R^1$ is phenyl, which is optionally substituted by halogen;
R is hydrogen or lower alkyl;
$R^2$ is lower alkyl, lower alkoxy, $CF_3$ or S-lower alkyl;
$R^3/R^{3'}$ are independently from each other hydrogen or lower alkyl;
or a pharmaceutically acceptable acid addition salt, a racemic mixture, or its corresponding enantiomer and/or optical isomer and/or stereoisomer thereof.

3. A compound of claim 2, selected from the group consisting of
2,2-Dimethyl-N-(5-phenylethynyl-pyridin-2-yl)-propionamide,
N-(5-Phenylethynyl-pyridin-2-yl)-butyramide,
Pentanoic acid (5-phenylethynyl-pyridin-2-yl)-amide,
3-Methyl-N-(5-phenylethynyl-pyridin-2-yl)-butyramide,
(RS)-2-Methyl-pentanoic acid (5-phenylethynyl-pyridin-2-yl)-amide,
2-Methylsulfanyl-N-(5-phenylethynyl-pyridin-2-yl)-acetamide,
2,2-Dimethyl-N-(5-phenylethynyl-pyrimidin-2-yl)-propionamide,
2,2,N-Trimethyl-N-(5-phenylethynyl-pyrimidin-2-yl)-propionamide,
2,2-Dimethyl-N-(6-phenylethynyl-pyridazin-3-yl)-propionamide,
2-Methoxy-N-(5-phenylethynyl-pyridin-2-yl)-acetamide,
N-[5-(3-Fluoro-phenylethynyl)-pyridin-2-yl]-2,2-dimethyl-propionamide,
2-Methoxy-2-methyl-N-(5-phenylethynyl-pyridin-2-yl)-propionamide,
N-[5-(3-Fluoro-phenylethynyl)-pyridin-2-yl]-2-methoxy-2-methyl-propionamide,
N-[5-(2,5-Difluoro-phenylethynyl)-pyridin-2-yl]-2-methoxy-2-methyl-propionamide,
N-[5-(3-Chloro-phenylethynyl)-pyridin-2-yl]-3,3,3-trifluoro-2,2-dimethyl-propionamide and
N-[6-(3-Chloro-phenylethynyl)-pyridazin-3-yl]-2,2-dimethyl-propionamide.

4. The compound of claim 1 having the formula

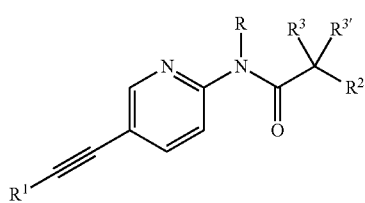

wherein
$R^1$ is phenyl or heteroaryl, which are optionally substituted by halogen, lower alkyl or lower alkoxy;
R is hydrogen or lower alkyl;
$R^2$ is hydrogen, lower alkyl, lower alkoxy, $CF_3$ or S-lower alkyl;
$R^3/R^{3'}$ are, independently from each other, hydrogen, lower alkyl or lower alkoxy;
 or $R^3$ and $R^{3'}$ form together a $C_{3-5}$-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

5. A compound of claim 4 selected from the group consisting of
2,2-Dimethyl-N-(5-phenylethynyl-pyridin-2-yl)-propionamide,
N-(5-Phenylethynyl-pyridin-2-yl)-butyramide,
Pentanoic acid (5-phenylethynyl-pyridin-2-yl)-amide,
3-Methyl-N-(5-phenylethynyl-pyridin-2-yl)-butyramide,
(RS)-2-Methyl-pentanoic acid (5-phenylethynyl-pyridin-2-yl)-amide,
2-Methylsulfanyl-N-(5-phenylethynyl-pyridin-2-yl)-acetamide,
2-Methoxy-N-(5-phenylethynyl-pyridin-2-yl)-acetamide,
N-[5-(3-Fluoro-phenylethynyl)-pyridin-2-yl]-2,2-dimethyl-propionamide, 2-Methoxy-2-methyl-N-(5-phenylethynyl-pyridin-2-yl)-propionamide,
N-[5-(3-Fluoro-phenylethynyl)-pyridin-2-yl]-2-methoxy-2-methyl-propionamide,
N-[5-(2,5-Difluoro-phenylethynyl)-pyridin-2-yl]-2-methoxy-2-methyl-propionamide and
N-[5-(3-Chloro-phenylethynyl)-pyridin-2-yl]-3,3,3-trifluoro-2,2-dimethyl-propionamide.

6. The compound of claim 1 having the formula

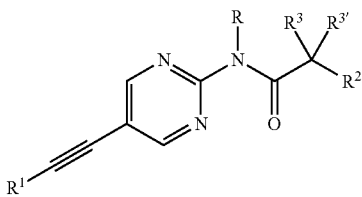

IB wherein
$R^1$ is phenyl or heteroaryl, which are optionally substituted by halogen, lower alkyl or lower alkoxy;
R is hydrogen or lower alkyl;
$R^2$ is hydrogen, lower alkyl, lower alkoxy, $CF_3$ or S-lower alkyl;
$R^3/R^{3'}$ are, independently from each other, hydrogen, lower alkyl or lower alkoxy;
or $R^3$ and $R^{3'}$ form together a $C_{3-5}$-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

7. A compound of claim 6 selected from
2,2-Dimethyl-N-(5-phenylethynyl-pyrimidin-2-yl)-propionamide or
2,2,N-Trimethyl-N-(5-phenylethynyl-pyrimidin-2-yl)-propionamide.

8. The compound of claim 1 having the formula

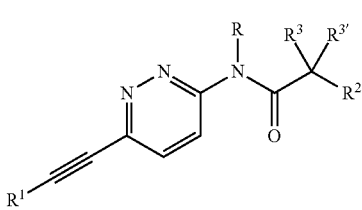

ID wherein
$R^1$ is phenyl or heteroaryl, which are optionally substituted by halogen, lower alkyl or lower alkoxy;
R is hydrogen or lower alkyl;
$R^2$ is hydrogen, lower alkyl, lower alkoxy, $CF_3$ or S-lower alkyl;
$R^3/R^{3'}$ are independently from each other hydrogen, lower alkyl or lower alkoxy;
or $R^3$ and $R^{3'}$ form together a $C_{3-5}$-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

9. A compound of claim 8, selected from
2,2-Dimethyl-N-(6-phenylethynyl-pyridazin-3-yl)-propionamide or
N-[6-(3-Chloro-phenylethynyl)-pyridazin-3-yl]-2,2-dimethyl-propionamide.

10. The compound of claim 1 having the formula

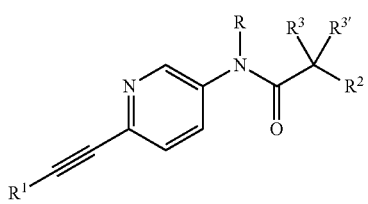

IE wherein
$R^1$ is phenyl or heteroaryl, which are optionally substituted by halogen, lower alkyl or lower alkoxy;
R is hydrogen or lower alkyl;
$R^2$ is hydrogen, lower alkyl, lower alkoxy, $CF_3$ or S-lower alkyl;
$R^3/R^{3'}$ are independently from each other hydrogen, lower alkyl or lower alkoxy;
or $R^3$ and $R^{3'}$ form together a $C_{3-5}$-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

11. The compound of claim 1 having the formula

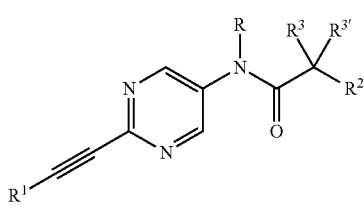

IF wherein
$R^1$ is phenyl or heteroaryl, which are optionally substituted by halogen, lower alkyl or lower alkoxy;
R is hydrogen or lower alkyl;
$R^2$ is hydrogen, lower alkyl, lower alkoxy, $CF_3$ or S-lower alkyl;
$R^3/R^{3'}$ are independently from each other hydrogen, lower alkyl or lower alkoxy;
or $R^3$ and $R^{3'}$ form together a $C_{3-5}$-cycloalkyl-, tetrahydrofuran- or an oxetane-ring;
or a pharmaceutically acceptable acid addition salt, a racemic mixture, or its corresponding enantiomer and/or optical isomer and/or stereoisomer thereof.

12. A process for preparation of a compound of claim 1 comprising a) reacting a compound of formula

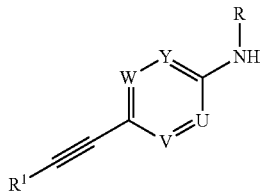

with a suitable compound of formula

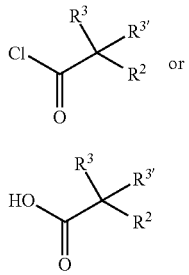

to a compound of formula

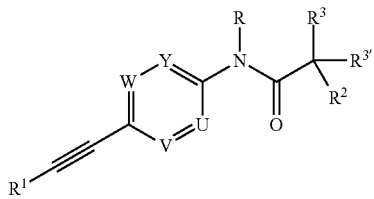

I wherein the substituents are defined in claim 1, or if desired, converting the compounds obtained into pharmaceutically acceptable acid addition salts, or b) reacting a compound of formula

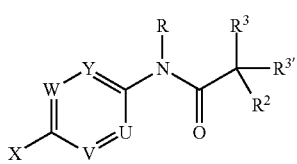

with a suitable compound of formula

2 to a compound of formula

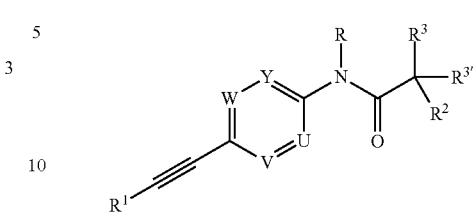

I wherein the substituents are defined in claim 1, or if desired, converting the compounds obtained into pharmaceutically acceptable acid addition salts, or c) reacting a compound of formula

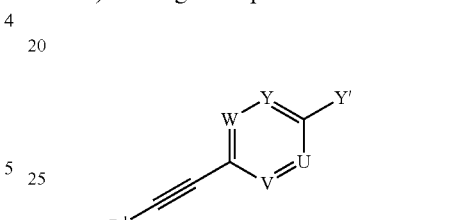

13 with a suitable compound of formula

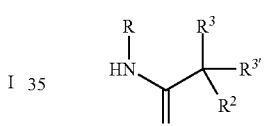

to a compound of formula

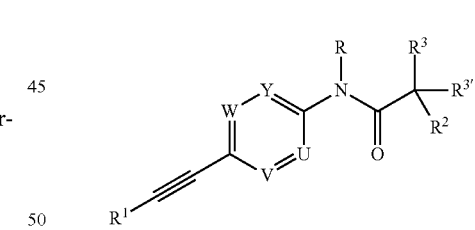

I wherein the substituents are defined in claim 1, or d) reacting a compound of formula

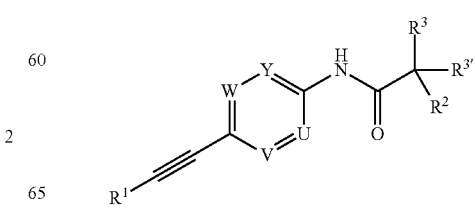

I-1 with a suitable compound of formula
R-hal
to a compound of formula

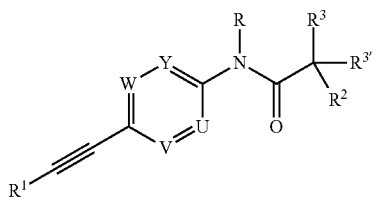

wherein R is alkyl and hal is halogen and wherein the other substituents are defined in claim 1, or if desired, converting the compounds obtained into pharmaceutically acceptable acid addition salts.

13. A pharmaceutical composition comprising a compound of claim 1 together with at least one therapeutically inert carrier.

* * * * *